United States Patent [19]

Frackleton et al.

[11] Patent Number: 5,133,937
[45] Date of Patent: Jul. 28, 1992

[54] ANALYSIS SYSTEM HAVING A REMOVABLE REACTION CARTRIDGE AND TEMPERATURE CONTROL

[75] Inventors: John J. Frackleton, Wilmington; James E. Rasmussen, Plainville; Lawrence Milesky, Needham, all of Mass.

[73] Assignee: Iniziative Marittime, 1991 S.R.L., Turin, Italy

[21] Appl. No.: 360,008

[22] Filed: Jun. 1, 1989

[51] Int. Cl.$^5$ .......................................... G01N 35/00
[52] U.S. Cl. .................................. 422/81; 422/67; 435/288; 435/289; 435/290; 436/52
[58] Field of Search .................. 422/81, 67, 289; 204/409; 436/52; 435/288, 286, 290

[56] References Cited

U.S. PATENT DOCUMENTS

| | | |
|---|---|---|
| 3,515,491 | 6/1970 | Emary. |
| 3,915,804 | 10/1975 | Messing. |
| 3,926,734 | 12/1975 | Gray. |
| 4,052,161 | 10/1977 | Atwood. |
| 4,066,365 | 1/1978 | Staunton. |
| 4,153,513 | 5/1979 | Edelmann et al. ............. 435/14 |
| 4,207,394 | 6/1980 | Aldridge, Jr. et al. .......... 435/291 |
| 4,367,041 | 1/1983 | Webb, Jr.. |
| 4,377,560 | 7/1981 | Gray et al. ...................... 422/81 |
| 4,420,564 | 12/1983 | Teuji et al. ..................... 204/405 |
| 4,443,407 | 4/1984 | Weinberg et al. ............... 422/68 |
| 4,476,005 | 10/1984 | Tokinaga. |
| 4,490,235 | 12/1984 | Calzi .............................. 204/411 |
| 4,525,765 | 6/1985 | Abe et al. ....................... 204/405 |
| 4,640,821 | 2/1982 | Mody et al. ..................... 422/81 |
| 4,759,828 | 7/1988 | Young et al. ................... 204/403 |

OTHER PUBLICATIONS

Leon, Luis P. "Continuous-Flow Analysis for Glucose in Serum, with Use of Hexokinase and Glucose-6--Phosphate Dehydrogenase Co-Immobilized in Tubular Form", Clin. Chem. 26/1, 123-129 (1980).

Pacakova, Vera "Use of the Clark Oxygen Sensor With Immobilized Enzymes for Determinations in Flow Systems", Analytica Chimica Acta, 159 (1984) pp. 71-79.

Gilford Instrument Laboratories, Inc., *Spectrophotometers*, "Stasar III", 1975, pp. 1.1-3.6.

*Primary Examiner*—Robert J. Hill, Jr.
*Assistant Examiner*—William Chan
*Attorney, Agent, or Firm*—Fish & Richardson

[57] ABSTRACT

An analysis system for analyzing a biological fluid or the like for a constituent of the interest includes metal body structure with sample flow path channel structure that serially interconnects heater chamber structure, recess structure for receiving a reaction chamber cartridge and an analysis region to which a measuring system is coupled. The reaction chamber cartridge preferably includes reaction chamber structure with an immobilized enzyme in the reaction chamber that is capable of converting the constituent of interest to a constituent detectable by the measuring system. Cooperating with the metal body structure is a transparent face plate structure which permits visual observation of the sample flow path in the metal body structure. Thermally coupled to the metal body immediately adjacent the analysis region are a temperature sensor that provides a temperature signal to a control unit and a thermal source that receives control signals from the control unit as a function of signals from the temperature system for stabilizing the temperature of the metal body structure (including the reaction chamber structure, the heater chamber and the analysis region) at a desired analysis temperature.

23 Claims, 5 Drawing Sheets

ANALYSIS SYSTEM HAVING A REMOVABLE REACTION CARTRIDGE AND TEMPERATURE CONTROL

This invention relates to analysis systems, and more particularly to systems for the analysis of parameters of biological fluids such as blood.

A variety of systems have been developed for the analysis of liquid samples. Frequently, in such systems, it is desirable that the analysis region be essentially chemically inert, as, for example, the sample to be analyzed may be diluted or mixed with a reactive reagent prior to analysis. Also, analytical reactions frequently are temperature sensitive, and for such reactions the temperature of the analysis region should be accurately controlled. Such systems are employed for the analysis of specific constituents of biological fluids such as serum, plasma or urine, a volume of the sample liquid to be analyzed being mixed with a prechosen reagent corresponding to one or more of the specific constituents of interest and then disposed in the analysis region for analysis. In particular analysis systems, an immobilized enzyme has been used to convert a constituent of interest in the sample to an ion detectable by an electrode such as a polarographic electrode or ion selective electrode, for example, urea may be enyzmatically converted to ammonium ions which are detectable by an ammonium electrode.

In accordance with one aspect of the invention, there is provided an analysis system for analyzing a biological fluid or the like for a constituent of the interest, the system including metal body structure with sample flow path channel structure that serially interconnects heater chamber structure, recess structure for receiving a reaction chamber cartridge and an analysis region to which a measuring system is coupled. The reaction chamber cartridge preferably includes reaction chamber structure with an immobilized enzyme in the reaction chamber that is capable of converting the constituent of interest to a constituent detectable by the measuring system. Cooperating with the metal body structure is a transparent face plate structure which permits visual observation of the sample flow path in the metal body structure. Thermally coupled to the metal body immediately adjacent the analysis region are a temperature sensor that provides a temperature signal to a control unit and a thermal source that receives control signals from the control unit as a function of signals from the temperature system for stabilizing the temperature of the metal body structure (including the reaction chamber structure, the heater chamber and the analysis region) at a desired analysis temperature.

In accordance with another aspect of the invention, there is provided a system for analyzing a biological fluid or the like for a constituent of interest that includes structure defining a sample inlet port, structure defining an analysis region, a measuring system in sensing relation to the analysis region, structure defining a recess for receiving a replaceable cartridge assembly that includes reaction chamber structure with an immobilized enzyme in the reaction chamber that is capable of converting the constituent of interest to a constituent of interest to a constituent detectable by the measuring system. In accordance with still another aspect of the invention, the replaceable cartridge assembly includes structure defining a reaction chamber with an immobilized enzyme therein, the reaction chamber including inlet and outlet ports and seal structure for sealing engagement with a flow path in the analysis cuvette to provide replaceable insertion of the reaction chamber structure in series in a flow path in the analysis cuvette.

In a particular embodiment, the reaction chamber has a volume of less than about 200 microliters and is in the form of an elongated tube (about twenty centimeters long) that is disposed in coil form on a metal temperature stabilizing cartridge body; glucose oxidase and urease enzymes are co immobilized on the inner surface of the tube; and resilient coupling structures carried by the temperature stabilizing cartridge body each includes a connector portion that receives an end of the tube, a seal portion that seats in sealing relation on a port of the analysis cuvette recess, and through passage between the connecter and seal portions of the coupling member. The analysis cuvette includes metal track plate structure with an outwardly open flow path channel in a planar surface thereof that is coated with a thermally conductive, corrosion resistant dielectric material. Against the planar body surface is seated a transparent urethane gasket member that is secured with a transparent acrylic face plate structure. A thermoelectric source is physically coupled to the surface of the track plate opposite the planar surface, a temperature sensor is embedded in the track plate adjacent an analysis region, and a control unit responsive to the temperature sensor operates the thermoelectric source to maintain the temperature of the track plate at 31° plus or minus 0.1° C.

The replaceable cartridge assembly is readily removed from the analysis cuvette to change or replace the reaction chamber as desired, and readily reinserted into the cartridge receiving recess with a body surface biased against a metal heat sink and the reaction chamber sealingly inserted into the sample flow.

BRIEF DESCRIPTION OF THE DRAWINGS

Other features and advantages of the invention will be seen as the following description of a particular embodiment progresses, in conjunction with the drawings, in which.

DESCRIPTION OF PARTICULAR EMBODIMENT

Figure 1:
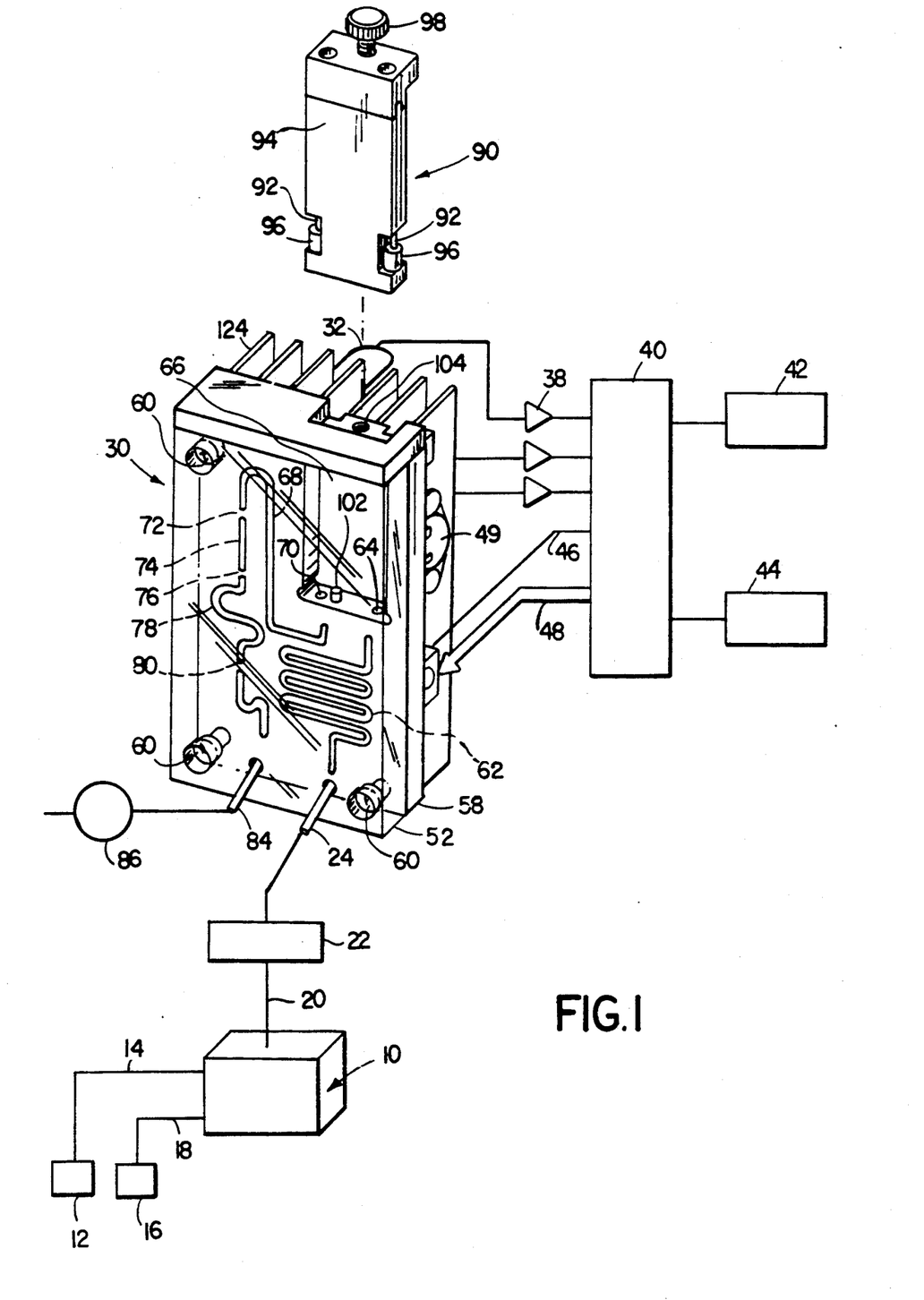
FIG. 1 is a perspective and diagrammatic view of an analysis system in accordance with the invention.
Figure 2:
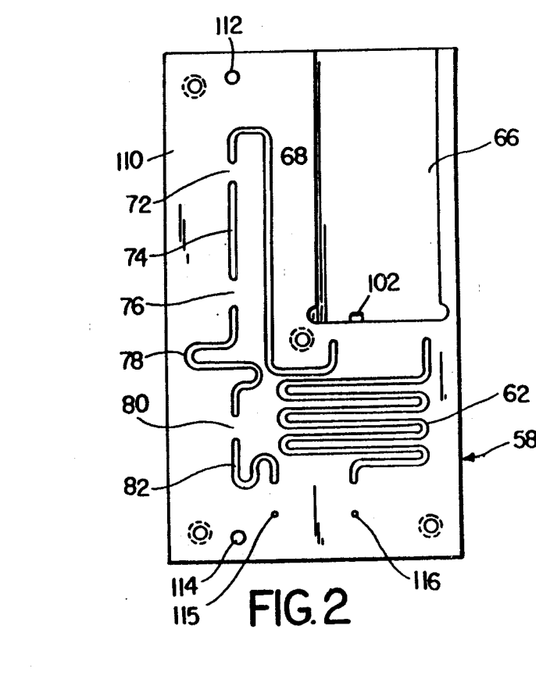
FIG. 2 is a front view of a track plate member of the cuvette assembly employed in the analysis system shown in FIG. 1.

The analysis system shown in FIG. 1 is of the type shown in commonly-assigned U.S. Pat. No. 4,997,627, filed Jul. 17, 1987, entitled "Sample Analysis", the disclosure of which is specifically incorporated herein by reference, and includes fluidics module 10 to which sample inlet station 12 is connected by conduit 14, and reservoir 16 for a reagent is connected by conduit 18. The sample and reagent are mixed at ambient temperature in module 10 and the resulting mixture is flowed over line 20 through preheater 22 (which raises the mixture temperature to about 29° C.) to inlet 24 of cuvette assembly 30. Coupled to cuvette assembly 30 are nonactin ionophor ammonium sensing electrode 32, oxygen sensing electrode 34 (FIG. 5) and reference electrode 36 (FIG. 5) that are connected via corresponding operational amplifiers 38 to control unit 40 for data interpretation and transfer of data resulting to output device 42 such as a display. A keyboard-type operator control 44 is coupled to control unit 40, and control unit 40 receives temperature signals from cuvette assembly 30 over lines 46 and provides control signals over lines 48 through thermostat 49 to thermoelectric heat pump assembly 50 in cuvette assembly 30.

Cuvette assembly 30 includes face plate 52 (FIGS. 9-11) of transparent acrylic that has a recess 54 (FIGS. 6 and 10) in which transparent urethane gasket 56 is received. Face plate 52 is seated against aluminum track plate member 58 (FIGS. 2-5) and secured by fasteners 60. Inlet 24 is connected to channel 62 that extends to port 64 in the base of cartridge receiving recess 66 that is formed in track plate 58. Coupling channel 68 extends from port 70 in the base of recess 66 to analysis region 72 for ammonium sensor 32; coupling channel 74 in track plate 58 connects analysis region 72 to analysis region 76 for oxygen sensor 34; serpentine isolation channel 78 connects analysis region 76 to analysis region 80 for reference electrode 36; and isolation loop channel 82 connects analysis region 80 to outlet 84 that in turn is connected to positive displacement piston pump 86.

Figure 13:
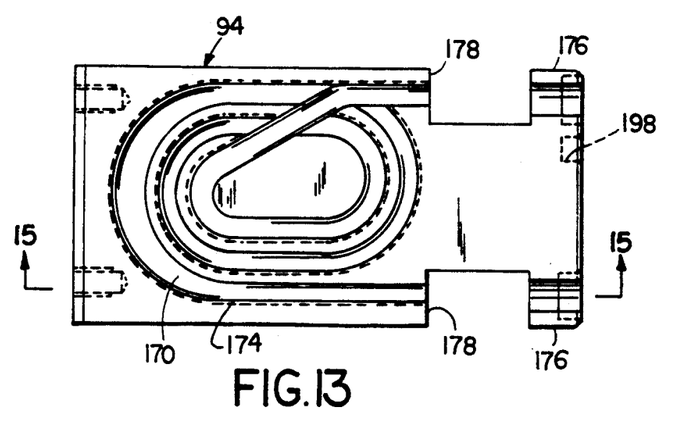
FIG. 13 is a top plan view of the body member of the cartridge shown in FIG. 12.
Figure 14:
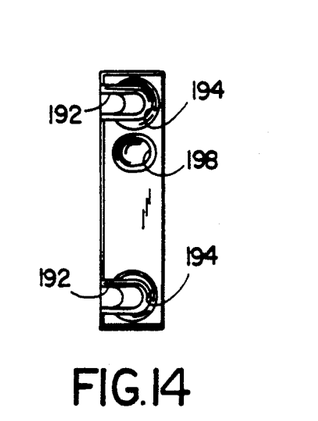
FIG. 14 is an end view of the body member shown in FIG. 13.

Replaceable cartridge 90 carries a nylon reaction chamber tube 92 that is about twenty centimeters long and has a capacity of about 115 microliters and is secured in spiral form on aluminum cartridge body 94. Urease and glucose oxidase enzymes are co-imobilized on the inner surface of nylon tube 92. Tube 92 is seated in a groove 170 (FIG. 13) formed in aluminum body 94. Resilient coupling elements 96 connect the ends of tube 92 to ports 64 and 68 when cartridge 90 is secured in cavity 66 by fastener structure 98 that cooperates with threaded bore 104 in the top wall of track plate 58. Post 102 in the base of cavity 66 cooperates with recess 196 (FIG. 13) cartridge 90 and provides cartridge alignment.

Figure 3:
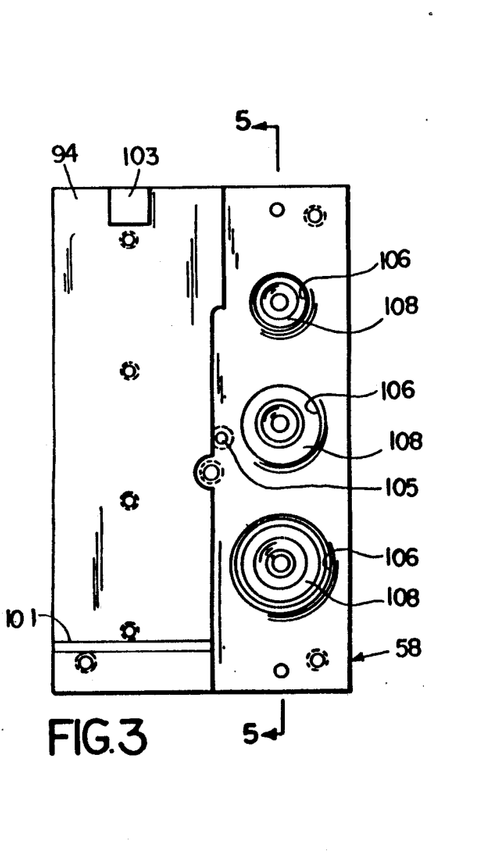
FIG. 3 is a rear view of the track plate shown in FIG. 2.
Figure 4:
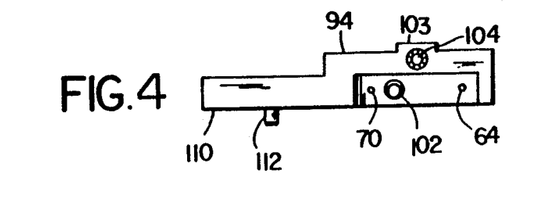
FIG. 4 is a top view of the track plate shown in FIG. 2.
Figure 5:
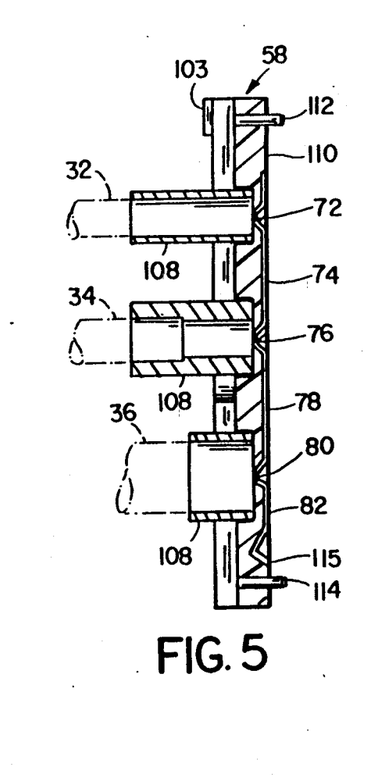
FIG. 5 is a sectional view taken along the line 5—5 of FIG. 3.

Further details of aluminum track plate 58 may be seen with reference to FIGS. 2-5. Plate 58 has a width of about six centimeters, a height of about ten centimeters, a thickness of about one centimeter in the vicinity of cartridge recess 66 and a thickness of about six millimeters in the vicinity of analysis regions 72, 76 and 80. Such relative thicknesses can be seen in the view of FIG. 4. Boss 103 projects from the rear surface of plate 58; recess 101 receives thermistor conductors 46; recess 105 receives temperature sensing thermistor 132, and recesses 106 aligned with analysis regions 72, 76 and 80 receive electrode housing members 108 as indicated in FIGS. 3 and 5. Front surface 110 of track plate 58 is coated with an inert, nonreactive pinhole free, thermally conductive, dielectric polymer (polyparaxylylene - Parylene) layer of about 0.03 millimeter thickness. Locating pins 112, 114 project from the front surface 110 of plate 58. Coated heater groove 62 has a width of about 0.8 millimeter, a depth of about 0.9 millimeter with a smoothly radiused base surface, and a length of about eighteen centimeters from inlet port 116 to outlet port 64 in the base surface 118 of recess 66. The other grooves 68, 74, 76 and 82 in track plate surface 110 are of similar cross sectional configuration, and of shape as indicated in the sectional view of FIG. 5, and are also coated with Parylene.

Figure 6:
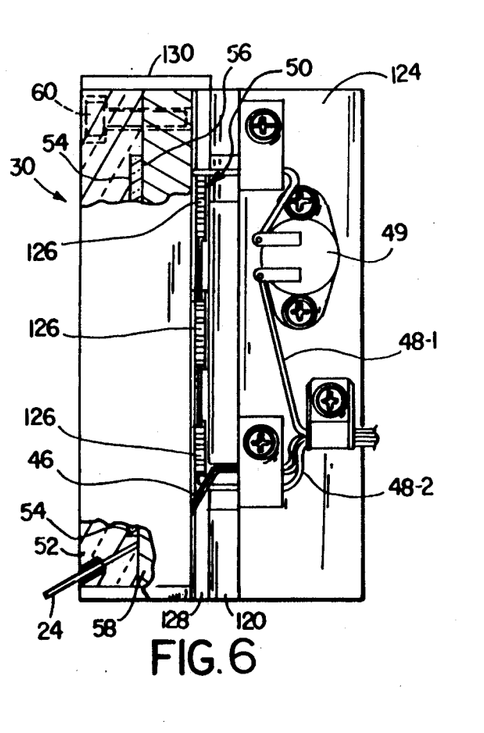
FIG. 6 is a side view of the cuvette assembly employed in the analysis system shown in FIG. 1.
Figure 7:
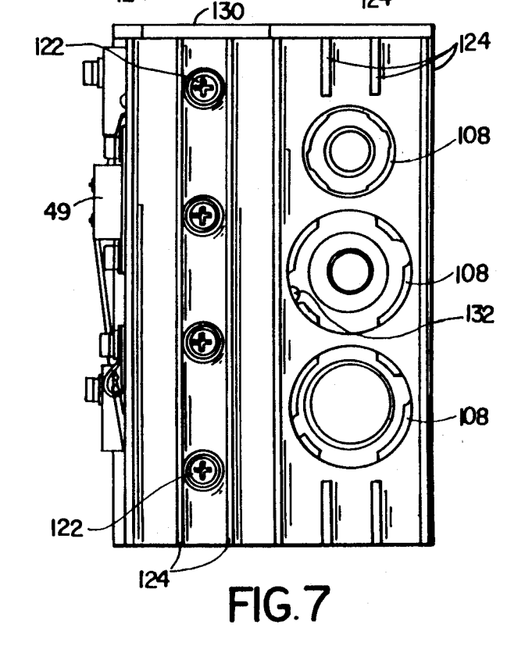
FIG. 7 is a rear view of the cuvette assembly shown in FIG. 6.
Figure 8:
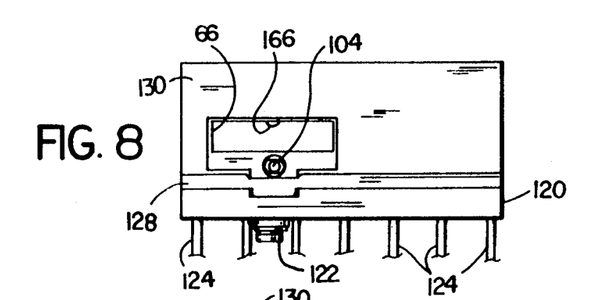
FIG. 8 is a top view of the cuvette assembly shown in FIG. 6.

With reference to the views of cuvette assembly 30 shown in FIGS. 6-8, track plate 58 is secured to heat sink block 120 with fasteners 122. The width and height of heat sink block 120 are similar to those dimensions of track plate 58, and the body of block 120 is about 0.6 centimeter thick with three centimeter long radiating fins 124 (fins 124 being broken off in FIG. 8) extending therefrom. Mounted on the side surface of a fin 124 of heat sink block 120 is thermostat 49 and clamped between heat sink block 120 and track plate 58 is an assembly 50 of three 12-watt maximum capacity thermoelectric heat pump units 126 (Material Electronic Product Corporation Part No. CP1.0-63-06L) that are interconnected in series with thermostat 49 between control unit lines 48-1 and 48-2. The heat pump units 126 are sandwiched between and are in thermal contact with heat sink 120 and track plate 58 (their cold faces being thermally coupled to track plate 58 and their hot faces being thermally coupled to heat sink 120); silicone rubber fiberglass reinforced insulator sheet 128 surrounds the heat pump units 126; and similar insulator sheets 130 are provided on the side and end surfaces of the track plate - face plate assembly. Thermistor 132 is secured in a recess 105 in track plate 58 immediately adjacent oxygen sensing electrode 34.

Figure 9:
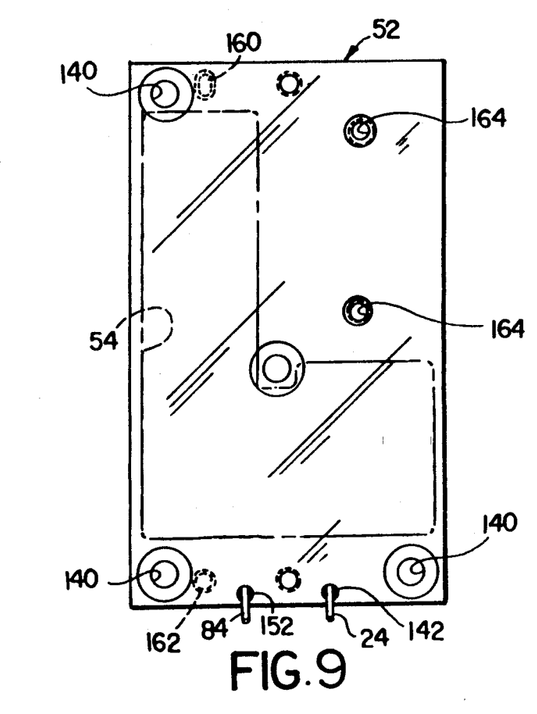
FIG. 9 is a front view of the face plate member of the cuvette assembly shown in FIG. 6.
Figure 10:
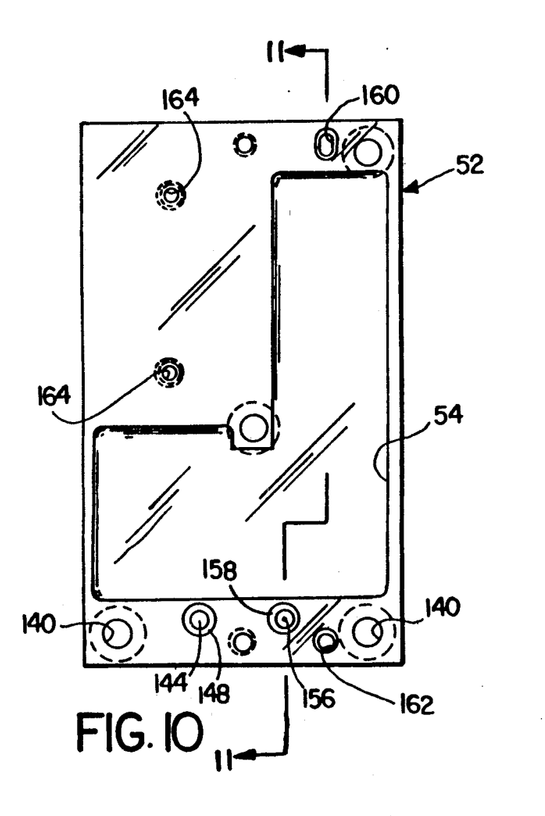
FIG. 10 is a rear view of the face plate shown in FIG. 9.
Figure 11:
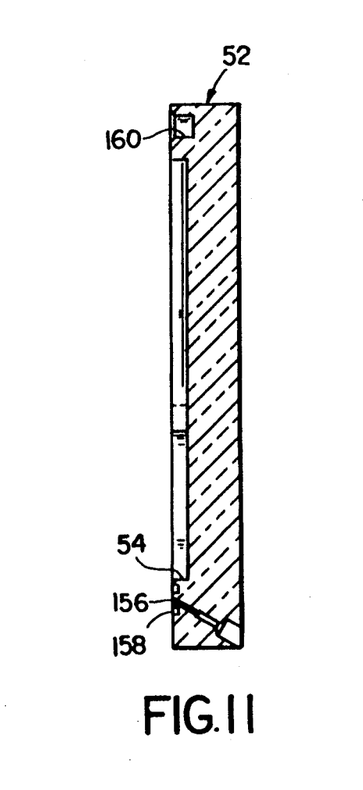
FIG. 11 is a sectional view taken along the line 11—11 of FIG. 10.

Further details of face plate 52 may be seen with reference to FIGS. 9-11. Face plate 52 is of clear acrylic and is secured to track plate 58 with fasteners 50 that pass through holes 140. Inlet line 24 is secured in port 142. An inclined passage in face plate 52 extends to port 144 on the rear surface 146 of face plate 52 that is surrounded by groove 148 that receives a sealing O-ring 150 as indicated in FIG. 6. Similarly, outlet line 84 is secured in recess 152 and communicates through inclined passage 154 to port 156 in the rear surface 146 of face plate 52 that is surrounded by O-ring receiving groove 158. Recess 160 receives track plate locating pin 112; and recess 162 receives locating pin 114. Formed in face plate 52 is recess 56 that is about three millimeters deep and receives clear urethane gasket 54 that has a thickness about 0.1 millimeter greater than the depth of recess 56 such that gasket 54 overlies and is compressed to form a transparent outer boundary of the flow passage defined by the grooves 62, 68, 74, 76 and 82 in track plate 58. Also carried by face plate 52 in apertures 164 are two spring biased ball plungers 166 (FIG. 8) that provide frictional resistance and positively seat cartridge 90 against the metal wall surface of cartridge recess 66.

Figure 15:
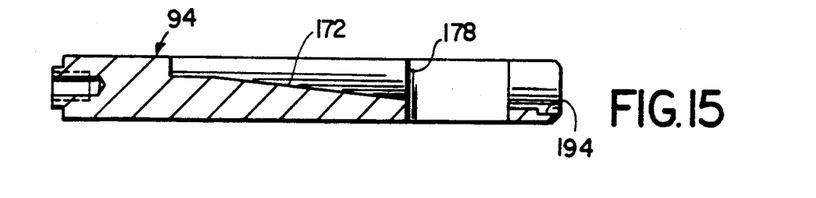
FIG. 15 is a sectional view taken along the line 15—15 of FIG. 13.
Figure 16:
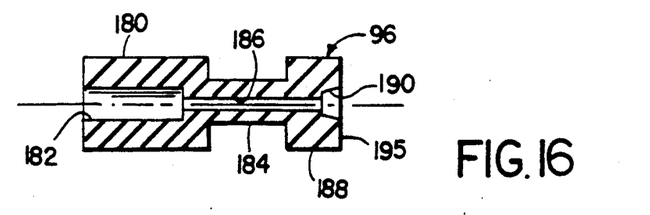
FIG. 16 is a sectional view of a coupling member employed in the cartridge assembly shown in FIG. 12.

Further details of cartridge 90 may be seen with reference to FIGS. 12-16. That cartridge includes aluminum body 94 that has a length of about five centimeters and a width of about 2.5 centimeters. Formed in the upper surface of body 94 is a spiral groove 170 that has an inclined base 172 (as indicated in FIG. 15) and tube retaining lip structure 174 at its upper edge. The ends of reaction chamber tube 92 are inserted into resilient couplings 96 and tube 92 is inserted into groove 170 in spiral configuration and couplings 96 are secured in tab portions 176 at the end of body 94 that are spaced about one centimeter from end surface 178 of the tube receiving groove portion of body 94.

Figure 12:
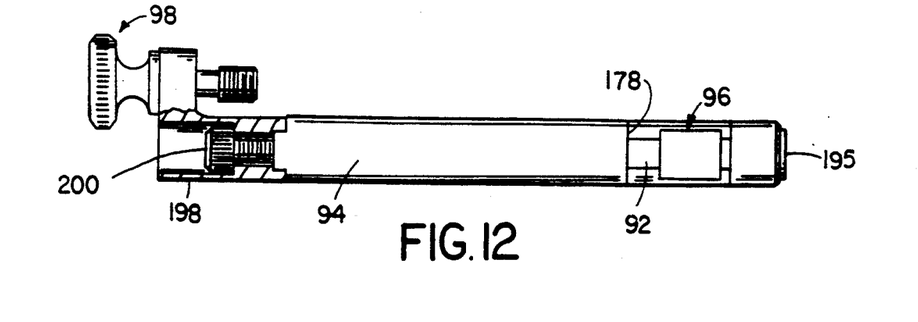
FIG. 12 is a side view of the replaceable cartridge assembly employed in the analysis system shown in FIG. 1.

Each seal coupling 96 is of 50 durometer black EP rubber and has a length of about 1.25 centimeters with a body portion 180 of about 0.6 centimeter length and one half centimeter diameter with cylindrical recess 182 that receives an end of reaction chamber tube 92; a reduced diameter connector portion 184 of about 0.4 centimeter length with a through passage 186 of about one millimeter diameter; and a seal portion 188 into which passage 186 extends and terminates in a flared port 190 that has an end diameter of about two millimeters. Seal portion 188 of coupling 96 is received in slot 192 and seated on surface 194 so its end surface 195 projects beyond end body tab 176 as indicated in FIG. 12. Delrin cap 198 carries fastener 98 and is secured to aluminum body 94 by bolts 200.

The reaction chamber cartridge 90 is replaceably inserted into the cuvette assembly 30 and secured by fastener 98 with the end surfaces 195 of the seal members 96 seated against and compressed in sealing relation on ports 64 and 70 to complete a series flow circuit between serpentine heater 62 and isolation channel 68. Cartridge 90 permits ready replacement of the reaction chamber 92 as desired.

In system operation, track plate 58 is maintained at a temperature of 31°±0.1° C. by control unit 40 that responds to signals from thermistor 132 and operates the thermoelectric units 126. Specified volumes of sample to be analyzed and acidic reagent are transferred into mixing module 10. After mixing, one milliliter volume syringe pump 86 is operated to pull the sample reagent mixture from module 10 through preheater 22, Parylene coated serpentine heater channel 62 and reaction chamber coil 92 into the Parylene coated analysis and reference channel regions 72, 76 and 80 of the electrode 32, 34, 36 at a flow rate of about 200 microliters per second. In this condition, a first portion of the sample mixture is at the 31° C. analysis temperature and in contact with the ammonium, oxygen and reference electrodes 32, 34, 36 while the reaction chamber coil 92, which is also at the 31° C. analysis temperature, is filled with a second portion of the sample reagent mixture and is in contact with the coimmobilized urease and glucose oxidase enzymes. Because of the rapid flow of the diluted sample through the reaction chamber 92, the diluted sample portion contacting electrodes 32, 34 and 36 contains unconverted sample that has not been acted upon by the enzymes to convert urea to ammonium ions and to convert glucose to hydrogen peroxide.

Pump 86 is then operated in bidirectional mode (alternate forward and backward directions of piston movement) to oscillate the diluted sample portions in the reaction chamber 92 and the analysis regions 72, 76 and 80 back and forth over a distance of about two centimeter. This bidirectional flow mode promotes enzyme - sample contact within reaction chamber 92 and equilibration at electrodes 32, 34 and 36. The bidirectional mode of operation of pump 86 is then terminated and the outputs from electrodes 32, 34, 36 are recorded by control unit 40 to provide first (pre-enzymatic reaction) sample data values.

Following acquisition of these first data values, and after glucose and oxygen in the second diluted sample portion has reacted with the immobilized glucose oxidase enzyme to form gluconic acid and hydrogen oxide, and urea in the second diluted sample portion has reacted with the immobilized urease enzyme to form ammonium ions and carbon dioxide, pump 86 is operated in unidirectional flow mode to pull the second diluted sample portion from reaction chamber 92 into the analysis regions 72, 76 and 80 of electrodes 32, 34 and 36. Pump 86 is again operated in bidirectional flow mode to oscillate the second sample portion in alternate directions to promote electrode equilibration. After that equilibration interval, a second set of data readings are taken, that data including information on the apparent oxygen and ammonium concentrations in the converted sample mixture.

After the second set of data is collected, pump 86 is operated in unidirectional flow mode to discard the sample to waste and the flow path is washed with buffer solution. The two sets of data provide pre-enzymatic reaction (background) measurements representing interferring contribution to electrode response; and post enzymatic reaction measurements.

Cartridge 90 is readily removed from cuvette assembly 30 to change or replace the reaction chamber tube 92 as desired, and readily reinserted into cavity 66 with its upper body surface biased against heat sink 120 by biasing members 166, and reaction chamber tube 92 sealingly connected in the series flow path by resilient couplings 96.

While a particular embodiment of the invention has been shown and described, various modifications will be apparent to those skilled in the art, and therefore it is not intended that the invention be limited to the disclosed embodiment, or to details thereof, and departures may be made therefrom within the spirit and scope of the invention.

What is claimed is:

1. An analysis system for analyzing a biological fluid or the like for a constituent of interest comprising
   metal body structure defining an inlet port, a heater chamber, an analysis region, recess structure for receiving a reaction chamber cartridge, and passage structure for serially interconnecting said heater chamber, said recess structure and said analysis region, said passage structure including an outwardly open flow path channel in a planar surface of said metal body structure, said channel being coated with a thermally conductive, corrosion resistant dielectric material, and further including a transparent gasket member seated against said planar surface of said metal body structure,
   a thermal source thermally coupled to said metal body structure immediately adjacent said analysis region and a temperature sensor thermally coupled adjacent said analysis region for providing a temperature signal to a control unit, said thermal source responding to control signals as a function of signals from said temperature sensor to stabilize the temperature of said metal body structure, and
a replaceable reaction chamber cartridge for releasable insertion into said recess structure for connection in series between said heater chamber and said analysis region for modifying a constituent of interest in the sample of biological fluid to be analyzed.

2. The system of claim 1 wherein said thermal source is a thermoelectric unit that is physically coupled to a surface of said metal body structure and said temperature sensor is a thermistor embedded in said metal body structure adjacent said analysis region.

3. The system of claim 2 further includes heat sink structure spaced from said metal body structure, and wherein said thermoelectric unit has a hot face and a cold face, said cold face being thermally coupled to said metal body structure and said hot face being thermally coupled to said heat sink structure.

4. The system of claim 1 wherein said analysis region and said reaction chamber are connected in a series flow path, and said liquid flow means includes a positive displacement pump that is connected to said liquid flow path.

5. The system of claim 1 further includes a measuring system in sensing relation to said analysis region, said measuring system includes two electrode devices for measuring different constituents of interest in said sample, at least one of said electrode devices being an ion selective electrode device.

6. The system of claim 1 wherein said constituent of interest is urea, and further includes a measuring system in sensing relation to said analysis region, said measuring system includes an ammonium selective electrode, and said reaction chamber includes immobilized urease enzyme.

7. The system of claim 1 wherein said reaction chamber cartridge includes reaction chamber structure with an immobilized enzyme in said reaction chamber that is capable of converting the constituent of interest to a constituent detectable at said analysis region.

8. The system of claim 7 wherein said constituent of interest is glucose, and further includes a measuring system in sensing relation to said analysis region, said measuring system includes an oxygen sensing electrode, and said reaction chamber includes immobilized glucose oxidase.

9. The system of claim 1 wherein said reaction chamber cartridge includes structure defining inlet and outlet ports and seal structure coupled to said inlet and outlet port structures for sealing engagement with a flow path in said metal body structure.

10. The system of claim 9 wherein said reaction chamber is in the form of an elongated tube; and said seal structure includes a seal member that includes a connector portion that receives an end of said tube, a seal portion, and a through passage between said connecter and seal portions of said seal member.

11. The system of claim 9 wherein said reaction chamber cartridge includes a metal temperature stabilizing cartridge body, said reaction chamber has a volume of less than about two hundred microliters and is in the form of an elongated tube that is disposed in coil form on said metal temperature stabilizing cartridge body; glucose oxidase and urease enzymes are co-immobilized on the inner surface of said tube; and said seal structure is carried by said temperature stabilizing cartridge body.

12. The system of claim 11 further includes means for biasing said temperature stabilizing cartridge body against said metal body structure, and wherein said temperature sensor is a thermistor embedded in said metal body structure adjacent said analysis region.

13. A replaceable cartridge assembly for use in an analysis cuvette for analyzing a biological fluid for a constituent of interest that includes flow path structure extending from a sample inlet port through structure defining an analysis region to an outlet port, a measuring system in sensing relation to said analysis region, and structure in said flow path structure defining a recess,
said replaceable cartridge assembly being adapted to be releasably inserted as a unit into said recess, said cartridge assembly including a metal temperature stabilizing cartridge body with a planar surface, spiral channel structure in said planar surface of said cartridge body, a tubular reaction chamber in spiral coil form releasably received in said channel structure, said reaction chamber structure having an immobilized enzyme in said reaction chamber that is capable of converting the constituent of interest to a constituent detectable by said measuring system, said reaction chamber structure including structure defining inlet and outlet ports and seal structure coupled to said inlet and outlet port structures for sealing engagement with a flow path in said analysis cuvette to permit replaceable insertion of said reaction chamber structure in series in a flow path in said analysis cuvette.

14. The cartridge assembly of claim 13 wherein said reaction chamber has a volume of less than about two hundred microliters and is in the form of an elongated tube that is disposed in coil form on said metal temperature stabilizing cartridge body; and glucose oxidase and urease enzymes are co-immobilized on the inner surface of said tube.

15. The cartridge assembly of claim 13 wherein each said seal structure includes a connector portion that is connected to a said port structure, a seal portion that is adapted to seat in sealing relation on a port of said analysis cuvette recess, and a through passage between said connecter and seal portions of said seal structure.

16. A replaceable cartridge assembly for use in an analysis cuvette for analyzing a biological fluid for a constituent of interest that includes flow path structure extending from a sample inlet port through structure defining an analysis region to an outlet port, a measuring system in sensing relation to said analysis region, and structure in said flow path structure defining a recess,
said replaceable cartridge assembly being adapted to be releasably inserted as a unit into said recess, said cartridge assembly including
a metal temperature stabilizing cartridge body with a planar surface, spiral channel structure in said planar surface of said cartridge body for releasably receiving a tubular reaction chamber in spiral coil form,
an elongated tube disposed in spiral coil form in said spiral channel structure, said tube having inlet and outlet ports, seal members coupled to said inlet and outlet ports for sealing engagement with a flow path in said analysis cuvette to permit manual replaceable insertion of said cartridge assembly as a unit in series in said flow path in said analysis cuvette, each said seal member including a connector portion that is connected to a said port, a seal portion that is adapted to seat in sealing relation on a port of said analysis cuvette recess, and an intermediate portion that defines a through passage between said connecter and seal portions of said seal member and tab structure in said cartridge body for releasably receiving said intermediate portions of said seal members connected to said ports of said tubular reaction chamber.

17. A system for analyzing a biological fluid for a constituent of interest comprising analysis cuvette structure defining a sample inlet port, said analysis cuvette structure including metal track plate structure with an outwardly open flow path channel in a planar surface thereof that is coated with a thermally conductive, corrosion resistant dielectric material, and a transparent gasket member seated against said planar body surface, structure defining an analysis region, a measuring system in sensing relation to the analysis region, structure defining a recess, and passage structure defining a sample flow path between said inlet port structure and said recess and a sample flow path between said recess and said analysis region, and a replaceable cartridge assembly adapted to be releasably inserted as a unit into said recess, said cartridge assembly including a metal temperature stabilizing cartridge body with a planar surface, spiral channel structure in said planar surface of said cartridge body, a tubular reaction chamber in spiral coil form releasably received in said channel structure, said reaction chamber having an immobilized enzyme in said reaction chamber that is capable of converting the constituent of interest to a constituent detectable by the measuring system, and coupling structure for sealingly connecting said tubular reaction chamber to said passage structure when said replaceable cartridge assembly is in said recess.

18. The system of claim 17 and further including heat sink structure spaced from said metal track plate structure, a thermoelectric source physically coupled to said metal track plate structure and to said heat sink structure, a temperature sensor adjacent said analysis region, and a control unit responsive to said temperature sensor for operating said thermoelectric source to maintain the temperature of said metal track plate structure at about 30° C.

19. The system of claim 18 further includes heat sink structure and wherein said thermal source is a thermoelectric unit that has a hot face and a cold face, said cold face being thermally coupled to said metal track plate structure and said hot face being thermally coupled to said heat sink structure, and said temperature sensor is a thermistor embedded in said metal track plate structure adjacent said analysis region.

20. The system of claim 19 wherein said measuring system includes two electrode devices for measuring different constituents of interest in said sample, at least one of said electrode devices being an ion selective electrode device.

21. The system of claim 20 wherein said reaction chamber structure has a volume of less than about two hundred microliters and is in the form of an elongated tube that is disposed in coil form in said channel structure; glucose oxidase and urease enzymes are co-immobilized on the inner surface of said tube; and said coupling structure is carried by said temperature stabilizing cartridge body.

22. The system of claim 21 further includes means for biasing said temperature stabilizing cartridge body against said metal track plate structure.

23. The system of claim 17 wherein said coupling structure includes a seal member with a connector portion that is connected to said reaction chamber structure, a seal portion that has an end surface projecting beyond the end of said replaceable cartridge assembly, said end surface being adapted to seat in sealing relation on a port of said recess, and a through passage between said connector and seal portions of said seal member.

* * * * *